United States Patent
Jackson et al.

(10) Patent No.: US 12,338,209 B2
(45) Date of Patent: Jun. 24, 2025

(54) ASTAXANTHIN ESTERS AND METHODS OF USE THEREOF

(71) Applicant: CARDAX, INC., Honolulu, HI (US)

(72) Inventors: Henry L. Jackson, Honolulu, HI (US); Gilbert M. Rishton, Honolulu, HI (US)

(73) Assignee: CARDAX, INC., Honolulu, HI (US)

( * ) Notice: Subject to any disclaimer, the term of this patent is extended or adjusted under 35 U.S.C. 154(b) by 728 days.

(21) Appl. No.: 17/764,450

(22) PCT Filed: Sep. 25, 2020

(86) PCT No.: PCT/US2020/052840
§ 371 (c)(1),
(2) Date: Mar. 28, 2022

(87) PCT Pub. No.: WO2021/062237
PCT Pub. Date: Apr. 1, 2021

(65) Prior Publication Data
US 2022/0380306 A1   Dec. 1, 2022

Related U.S. Application Data

(60) Provisional application No. 62/907,025, filed on Sep. 27, 2019.

(51) Int. Cl.
*C07C 403/24* (2006.01)
*A61K 31/21* (2006.01)

(52) U.S. Cl.
CPC ................................. *C07C 403/24* (2013.01)

(58) Field of Classification Search
CPC .............................. C07C 403/24; A61K 31/21
See application file for complete search history.

(56) References Cited

U.S. PATENT DOCUMENTS 7,253,297 B2 * 8/2007 Gloor .................... A23K 20/179
560/190
7,723,327 B2 * 5/2010 Lockwood .............. C07F 9/117
514/473

FOREIGN PATENT DOCUMENTS

EP         1952845 A1 *  8/2008  ............. A61K 8/375

* cited by examiner

*Primary Examiner* — Sikarl A Witherspoon
(74) *Attorney, Agent, or Firm* — MARSHALL, GERSTEIN & BORUN LLP (57) ABSTRACT

Provided herein are tertiary amino ester derivatives of astaxanthin and methods of making the same and using the same, e.g., to improve inflammatory and/or cardiovascular health.

19 Claims, 1 Drawing Sheet

ASTAXANTHIN ESTERS AND METHODS OF USE THEREOF

BACKGROUND

Astaxanthin, a carotenoid, is a potent direct radical scavenger and singlet oxygen quencher and possesses many desirable qualities as a therapeutic agent for various disease for which radicals are implicated. However, astaxanthin can be difficult to formulate, can have low absorption, and solubility. Thus, derivatives or prodrugs of astaxanthin are attractive targets that may address some of the challenges of directly formulating and/or administering astaxanthin.

Coronary artery disease is the number one cause of mortality in the United States and many developed countries. The process of atherosclerosis begins in childhood and generally progresses with age. The rate and extent of progression vary per individual. Well-recognized conventional risk factors that increase the rate of progression include cigarette smoking, Diabetes Mellitus, hypertension, hyperlipidemia, and a family history of cardiovascular disease. Males are generally affected at a younger age than females ("Screening for asymptomatic coronary artery disease. U.S. Preventive Services Task Force.", Am Fam Physician. 1989 December; 40(6):99-104).

Inflammation has been recognized as a common mechanism for all of these risk factors, and as an independent marker, playing a key role in the development of atherosclerosis from the early stages through development of atherosclerotic plaques, instability, and rupture. A host of inflammatory health biomarkers are linked with this process, including CRP, TNF-$\alpha$, IL-1$\beta$, IL-6, and oxLDL. The JUPITER (Justification for the Use of Statins in Prevention, an Intervention Trial Evaluating Rosuvastatin) trial demonstrated that elevated CRP>2.0 mg/L is an independent risk factor for coronary events, even in subjects with LDL-C<130 mg/dL, and that reduction in CRP improved cardiac outcomes. The JUPITER trial randomized subjects to 20 mg/D of rosuvastatin vs. placebo. At enrollment, the median CRP was 4.2 mg/L, and patients who achieved a reduction in CRP<2.0 had a 62% reduction in vascular events. Published in 2009, the JUPITER trial results had a positive effect on the practice of clinical medicine, with more attention to CRP as a risk factor for cardiac events and broader use of statins (Ridker, P M, Circ Cardiovas Qual Outcomes. 2009; 2:279-285).

Because rosuvastatin lowers LDL-C as well as CRP, the medical community designed two large, multi-center, prospective, placebo controlled studies to further clarify whether reduction of inflammation reduces cardiac events in the absence of any effects on lipids.

Results were published in August 2017 from the CANTOS (Canakinumab ANti-inflammatory Thrombosis Outcome Study) trial (Ridker, P M, et al, N Engl J Med. 2017 Sep. 21; 377(12):1119-1131), comparing treatment with canakinumab vs. placebo for 48 months. Canakinumab is a monoclonal antibody that targets IL-1$\beta$, resulting in a reduction of IL-6 and CRP, but has no effect on LDL-C. This study enrolled 10,061 patients at multiple centers in 39 countries. Study patients had a history of previous myocardial infarction and CRP>2.0 mg/L, and were generally treated with standard of care therapy for hypertension, diabetes, hyperlipidemia, and anti-ischemics. Patients were randomized to treatment with placebo, 50 mg, 150 mg, or 300 mg of canakinumab injections every 3 months and followed for 48 months.

Data analysis showed that patients with active treatment noted a reduction in CRP and IL-6, with no change in lipids. The reduction in CRP noted at three months was generally maintained in the same range throughout the trial. The 150 mg treatment group had a 15% reduction in recurrent myocardial infarctions. Unfortunately, the active treatment groups had more deaths from infection (mostly tuberculosis) hence there was no net reduction in all-cause mortality. The results of the CANTOS trial are best understood by evaluating the response to therapy rather than the dose. Patients with CRP>2.0 mg/L (regardless of dose) at three months had results very similar to placebo recipients. Subjects with a reduction of CRP<2.0 mg/L (regardless of dose) had a 25% reduction in the primary end point (a composite of myocardial infarction, stroke, or cardiovascular death) and had a 31% reduction in cardiovascular death and all-cause mortality. These results were highly statistically significant. To further demonstrate the benefits of reducing inflammation, the best results were in patients with CRP<1.2 mg/L post-treatment.

Following publication of the results in August 2017, the response to the CANTOS trial was summarized as "one important step for clinical cardiology but a giant leap for vascular biology." (Baylis R A et al, Arterioscler Thromb Vasc Biol. 2017 November; 37(11):e174-e177). The "giant leap" is documented proof for the "inflammatory hypothesis," by demonstrating that patients with cardiac disease benefit from reduction of inflammation, even without any additional reduction in lipids, while being treated aggressively by conventional standard of care therapy. The "one important step" is a cautious assessment that canakinumab is unlikely to be widely used in a clinical setting, mostly due to the cost (currently about $16,000 per injection), the variable response, and concerns about the overall risk-to-benefit ratio. Reviewers also noted that canakinumab is a very narrow intervention, effecting only one target, and that other interventions with broader anti-inflammatory action should be explored.

A second large, multi-center, prospective, randomized, placebo controlled study was initiated about the same time as the CANTOS trial to evaluate the "inflammatory hypothesis." The CIRT (Cardiovascular Inflammation Reduction Trial) trial (Ridker et al., N Engl J Med 2019 February; 380: 752-762) initially planned to enroll 7,000 patients at 565 centers in the US and Canada, but the study was terminated for futility in April 2018 after enrollment of 4,786 patients at 417 centers. The population was somewhat broader than the CANTOS study, and included patients with CRP>2.0 mg/L and proven multi-vessel coronary artery disease plus either Diabetes Mellitus, Type II or metabolic syndrome as well as patients with a history of myocardial infarction. Patients were randomized to methotrexate at 15-20 mg/week vs. placebo. The results of the CIRT trial demonstrated that administration of methotrexate did not reduce levels of IL-1$\beta$, IL-6, or CRP and did not result in fewer cardiovascular events compared to placebo, providing further evidence of the importance of this pathway in the reduction of cardiovascular events. While this dose was considered to have a reasonable risk-to-benefit ratio in these patients, long term use is also associated with substantial toxicities including hepatic fibrosis or cirrhosis, myelosuppression, pulmonary damage, oral ulcers, and nausea, vomiting, or diarrhea.

There is a need for a safe, effective agent with broad mechanisms of action for maintenance of inflammatory health in subjects with cardiovascular risk factors, which can be used with conventional treatments without negative drug-study product interactions, and if it can also benefit lipid, metabolic, liver, and joint health.

SUMMARY

Provided herein are ester derivatives of astaxanthin. More particularly, provided is a compound or pharmaceutically acceptable salt thereof having a structure of In some cases, the compound or salt has a structure of In various cases, the compound is present as a salt form, e.g., as a hydrochloride salt and in some cases as a dihydrochloride salt.

Further provided herein is a composition comprising a compound or salt as disclosed herein and a pharmaceutically acceptable excipient. In various cases, the composition exhibits a stability that is better than that of a comparable composition comprising astaxanthin and/or another ester derivative of astaxanthin. In some cases, the stability is determined based upon measurement of degradation products after storage for a selected amount of time and optionally at high humidity and/or temperature.

Also provided are methods of preventing or treating cardiovascular disease (CVD) in a subject. In exemplary embodiments, the methods prevent or treat CVD by reducing C-reactive protein (CRP) levels. In exemplary embodiments, the method comprises administering a therapeutically effective amount of a compound or salt as disclosed herein to the subject. In some embodiments, the subject is one who also receives a standard of care for CVD or CVD risk management.

The present disclosure also provides methods of supporting cardiovascular health in a subject at risk for or suffering from CVD. In exemplary embodiments, the methods support cardiovascular health by reducing CRP levels. In exemplary embodiments, the method comprises administering a compound or salt as disclosed herein, e.g., a therapeutically effective amount of the compound or salt, to the subject. In some embodiments, the subject is one who also receives a standard of care for CVD or CVD risk management.

Further provided are methods of supporting inflammatory health in a subject at risk for or suffering from CVD. In exemplary embodiments, the methods prevent or treat CVD by reducing CRP levels. In exemplary embodiments, the method comprises administering a compound or salt as disclosed herein, e.g., a therapeutically effective amount of the compound or salt, to the subject. In some embodiments, the subject is one who also receives a standard of care for CVD or CVD risk management.

The present disclosure additionally provides methods of modifying levels of inflammatory health biomarkers or cardiovascular health biomarkers in a subject at risk for or suffering from CVD comprising administering a compound or salt as disclosed herein to the subject. In exemplary embodiments, the method (a) reduces levels of one or more of the following: TNF-$\alpha$, IL-1$\beta$, IL-6, INF-$\gamma$, oxidized LDL, total cholesterol, LDL cholesterol, VLDL cholesterol, triglycerides, HbA1c, ALT, AST, body weight, or blood pressure; and/or (b) increases levels of one or more of the following: FOXO3 activation or HDL cholesterol. In exemplary embodiments of such methods of modifying levels of biomarkers in a subject, the subject also receives standard of care for CVD or CVD risk management.

Also provided are methods of preparing a compound or salt as disclosed herein.

DETAILED DESCRIPTION

Provided herein are compounds, or pharmaceutically acceptable salts thereof, of astaxanthin esters. Astaxanthin, which has a structure of:

can be mono- or di-esterified at the one or each of its hydroxyl groups with an amino acid having a tertiary amine, e.g., a dimethyl amino acid. The two chiral centers of astaxanthin allow for two enantiomers ((S),(S) and (R),(R)) and a meso form ((R),(S)). In various cases, the astaxanthin is present as the (S),(S) form. In some cases, the astaxanthin is present as the meso form or the (R),(R) form. The amino acid can be a dimethyl amino version of any naturally occurring amino acid e.g., alanine, arginine, asparagine, aspartic acid, cysteine, glutamine, glutamic acid, glycine, histidine, isoleucine, leucine, lysine, methionine, phenylala-nine, serine, threonine, tryptophan, tyrosine, or valine, or a methyl amino version of proline. In some cases, the astaxanthin is mono-esterified with a dimethyl amino acid (or methyl amino proline). In some cases, the astaxanthin is di-esterified with two dimethyl amino acids (or methyl amino proline). The diester can be of two of the same dimethyl amino acid (or two methyl amino prolines), or two different dimethyl amino acids or methyl amino proline and a dimethyl amino acid.

In embodiments, the compound is a dimethyl amino glycine ester having a structure of In some cases, the compound or salt has a structure of which is the (S),(S) form. In some cases, the compound or salt thereof is in a (R),(R) form. In some cases, the compound or salt thereof is in a meso form (i.e., (R),(S) form).

The compound or salt can be prepared in a shorter synthetic route, in one step from astaxanthin, without need of protecting the amine (e.g., using a Boc protecting group). The product can be formed without subsequent need of protection group removal (e.g., strong acidic conditions to remove a Boc group). A coupling reaction between the astaxanthin and the amino acid can proceed with a cleaner reaction profile and faster rate for the synthesis, compared to a primary or secondary amino acid, such as a lysine or sarcosine derivative. Further, the compound or salt can be purified via recrystallization or slurrying (e.g., in acetone or dichloromethane) and not extensive purification techniques (e.g., column chromatography). With the amine present as a tertiary amine (e.g., substituted with two methyl groups), there is a reduced risk of intermediate imine formation or alkylation at the amine site. As such, a compound or salt thereof as disclosed herein can be obtained with a higher purity compared to an astaxanthin ester derivative having a primary or secondary amine that would require protection and subsequent deprotection (e.g., strong acidic conditions such as hydrochloric acid or trifluoroacetic acid).

In various cases, the compound is present as a pharmaceutically acceptable salt form. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66, 1-19, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N׳-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N׳-bis-dehydroabietylamine, glucamine, N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. In some cases, the compound as disclosed herein is present as a hydrochloride salt, and in some specific cases, as a dihydrochloride salt.

Pharmaceutical Compositions

In exemplary aspects of the present disclosure, the astaxanthin is part of a pharmaceutical composition when administered to the subject. The pharmaceutical composition comprising the compound as disclosed herein or salt thereof, in most aspects is purified and sterile. The term "purified" as used herein means having been increased in purity, wherein "purity" is a relative term, and not to be necessarily construed as absolute purity. In exemplary aspects, the purity of the compound (e.g., in the composition) is at least or about 50%, at least or about 60%, at least or about 70%, at least or about 80%, at least or about 90%, at least or about 95%, or at least or about 98% or is about 100%. In exemplary aspects, the pharmaceutical composition comprises a pharmaceutically acceptable carrier. As used herein, the term "pharmaceutically acceptable carrier" includes any of the standard pharmaceutical carriers, such as a phosphate buffered saline solution, water, oil, emulsions such as an oil/water or water/oil emulsion, and various types of wetting agents. The term also encompasses any of the agents approved by a regulatory agency of the US Federal government or listed in the US Pharmacopeia for use in animals, including humans. The pharmaceutical composition can comprise any pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety.

In exemplary aspects, the pharmaceutical composition comprises formulation materials that are nontoxic to recipients at the dosages and concentrations employed. In specific embodiments, pharmaceutical compositions comprising an active agent and one or more pharmaceutically acceptable salts; polyols; surfactants; osmotic balancing agents; tonicity agents; anti-oxidants; antibiotics; antimycotics; bulking agents; lyoprotectants; anti-foaming agents; chelating agents; preservatives; colorants; analgesics; or additional pharmaceutical agents. In exemplary aspects, the pharmaceutical composition comprises one or more polyols and/or one or more surfactants, optionally, in addition to one or more excipients, including but not limited to, pharmaceutically acceptable salts; osmotic balancing agents (tonicity agents); anti-oxidants; antibiotics; antimycotics; bulking agents; lyoprotectants; anti-foaming agents; chelating agents; preservatives; colorants; and analgesics.

In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

The pharmaceutical compositions can be formulated to achieve a physiologically compatible pH. In some embodiments, the pH of the pharmaceutical composition can be for example between about 4 or about 5 and about 8.0 or about 4.5 and about 7.5 or about 5.0 to about 7.5. In exemplary embodiments, the pH of the pharmaceutical composition is between 5.5 and 7.5.

In exemplary aspects, the pharmaceutical composition comprises free-flowing particles or beadlets (e.g., microbeadlets) comprising compound as disclosed herein or salt thereof. In exemplary aspects, the pharmaceutical composition comprises a gelatin capsule or a vegetable-based capsule (e.g., a tapioca capsule or a vegetable cellulose capsule) comprising free-flowing particles or beadlets (e.g., microbeadlets) comprising compound as disclosed herein or salt thereof. In exemplary aspects, the pharmaceutical composition additionally comprises one or more antioxidants. In exemplary instances, the pharmaceutical composition additionally comprises one or more of: modified food starch, corn starch, glucose syrup, sodium ascorbate, and DL-alpha-tocopherol. In some instances, compound as disclosed herein or salt thereof is dispersed in a corn-starch coated matrix of modified food starch and glucose syrup with sodium ascorbate and DL-alpha-tocopherol. In exemplary aspects, the pharmaceutical composition comprises a gelatin capsule or a vegetable-based capsule comprising free-flowing particles or beadlets (e.g., microbeadlets) comprising compound as disclosed herein or salt thereof dispersed in a corn-starch coated matrix of modified food starch and glucose syrup with sodium ascorbate and DL-alpha-tocopherol.

In exemplary aspects, the pharmaceutical composition comprises: (a) compound as disclosed herein or salt thereof, modified food starch, corn starch, glucose syrup, sodium ascorbate, DL-alpha-tocopherol, microcrystalline cellulose, tapioca capsule; (b) compound as disclosed herein or salt thereof, modified food starch, corn starch, glucose syrup, sodium ascorbate, DL-alpha-tocopherol, microcrystalline cellulose, vegetable stearate, vegetable cellulose capsule; (c) compound as disclosed herein or salt thereof, modified food starch, corn starch, glucose syrup, sodium ascorbate, DL-alpha-tocopherol, microcrystalline cellulose, vegetable stearate, vegetable cellulose capsule, titanium dioxide; (d) compound as disclosed herein or salt thereof, modified food starch, corn starch, glucose syrup, sodium ascorbate, DL-alpha-tocopherol, microcrystalline cellulose, vegetable stearate, gelatin capsule, FD&C blue #1, titanium dioxide.

With regard to the present disclosure, the compound or salt thereof, or pharmaceutical composition comprising the same, can be administered to the subject via any suitable route of administration. For example, the active agent can be administered to a subject via parenteral, nasal, oral, pulmonary, topical, vaginal, ocular, or rectal administration. In exemplary embodiments, the compound or salt thereof, or pharmaceutical composition comprising the same, is administered orally. The following discussion on routes of administration is merely provided to illustrate exemplary embodiments and should not be construed as limiting the scope in any way.

Formulations suitable for oral administration can consist of (a) liquid solutions, such as an effective amount of compound or salt dissolved or dispersed in diluents, such as water, saline, oil, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the compound or salt thereof in a flavor, usually sucrose and acacia or tragacanth, as well as pastilles comprising the compound or salt thereof in an inert base, such as gelatin and glycerin, or sucrose and acacia, emulsions, gels, and the like containing, in addition to, such excipients as are known in the art.

In exemplary embodiments, the compound or salt thereof is administered orally to the subject. In exemplary aspects, the compound or salt thereof is a tablet or capsule or caplet.

The pharmaceutical composition in exemplary aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., *J Pharm* 374: 46-52 (2009) and International Patent Application Publication Nos. WO 2008/130158, WO2004/033036; WO2000/032218; and WO 1999/040942.

The instant compositions may further comprise, for example, micelles or liposomes, or some other encapsulated form, or may be administered in an extended release form to provide a prolonged storage and/or delivery effect.

The disclosed pharmaceutical composition may be administered according to any regimen including, for example, daily (1 time per day, 2 times per day, 3 times per day, 4 times per day, 5 times per day, 6 times per day), three times a week, twice a week, every two days, every three days, every four days, every five days, every six days, weekly, bi-weekly, every three weeks, monthly, or bi-monthly.

In some aspects, the compound or salt as disclosed herein, or the pharmaceutical composition comprising the same, is taken on an empty stomach or after a period of fasting. In alternative aspects, the compound or salt as disclosed herein is administered with food, or within about 30 minutes after food (e.g., a meal).

Shelf Life and Stability

The compositions, comprising a compound or salt as disclosed herein, are generally stable upon storage, meaning that the compound or salt does not degrade or metabolize or epimerize. The shelf life of the composition at a selected storage condition at a selected storage time provides the compound or salt in an amount of at least 70% (by weight) of the starting compound or salt in the composition, or at least 75%, at least 80%, at least 85%, at least 90%, at least 95%, at least 98%, or at least 99% by weight. In some cases, if the compound or salt thereof is present initially as the (S), (S) form, the stability of the compound or salt thereof or composition thereof is assessed by measuring the epimerization of the compound or salt upon storage to (S), (S) form or meso form.

The composition can be stored at −20° C. to 30° C., e.g., −4 C, 0 C, 10° C., 15° C., 20° C., or 25° C. The composition can be stored for at least a week before assessing the amount of compound or salt still remaining in the composition, or at least 2 weeks, at least 3 weeks, at least a month, at least two months, at least 3 months, at least 4 months, at least five months, at least 6 months, or at least a year.

In embodiments, the compositions of the compounds or salts as disclosed herein have a greater stability than a composition of a secondary or primary amine ester derivative thereof (e.g., sarcosine, disarcosine, lysine, or dilysine ester), or salt of the ester derivative. In various cases, the stability of a compound is assessed by performing a stability test and comparing a purity of the compound to a purity the compound prior to the stability test. The change in purity can be expressed as a change in percentage of the purity of the compound. In various cases, the stability of a composition is assessed by performing a stability test and comparing the amount of the compound in the composition to an amount of the compound prior to the stability test. The change in compound due to degradation can be expressed as a change in percentage of the amount of compound in the composition. Examples of stability tests include, but are not limited to, a hydrolytic solution stability study and storage at ambient conditions. In some cases, the stability of the tertiary amine ester compounds or salts disclosed herein can be assessed by comparing the change in purity and/or the change in the amount of the tertiary amine ester compounds or salts compared to the change in purity and/or the change in the amount of the tertiary amine ester compounds or salts in similar secondary or primary amines. In some cases, the stability of the tertiary amine ester compounds or salts disclosed herein can be assessed by comparing the change in purity and/or the change in the amount of the tertiary amine ester compounds or salts compared to the initial purity and/or initial amount of the compounds.

A degradant can be, e.g., via cyclization, which forms a cyclized byproduct, as discussed below. Without being bound to theory, it is hypothesized that the substitution of a tertiary amine in place of a primary or secondary amine, as in the case of the dimethyl amino acid ester (e.g., dimethyl amino glycine), allows for the stability of the compound alone or in a composition in comparison to an astaxanthin ester possessing a primary or secondary amine, such as in the disarcosine ester. The proposed mechanism of instability for primary or secondary amines is shown in the below scheme. This instability is suppressed by a sterically hindered and relatively unreactive tertiary amine.

Scheme

Astaxanthin di-conjugate 2 (Asta-Sarc$_2$)

Methods of Use

The compounds or salt disclosed herein are useful as a therapeutic. The compound or salt, upon administration, can be converted to astaxanthin via hydrolysis of the ester bond. Astaxanthin has a number of physiological benefits, including in cardiovascular diseases, metabolic diseases, liver disease, arthritis, and aging. Astaxanthin has been shown to have biological activity as follows: decreases CRP, decreases triglycerides, decreases LDL-C, increases HDL-C, decreases apolipoprotein B, increases adiponectin, decreases blood pressure (systolic and diastolic), increases blood flow velocity, decreases IL-6, decreases re-thrombosis, decreases atherosclerosis, decreases cholesterol, increases nitric oxide production, decreases TNF-α, decreases oxidative stress (increases MDA, IsoP, SOD, TAC), decreases fasting blood glucose levels, increases insulin levels and sensitivity (HOMA-IR and QUICK increases), increases insulin response, increases glucose tolerance (ipGTT), increases GLUT-4 translocation, increases JNK and/or ERK-1 levels, decreases NASH disease markers (e.g., steatosis, nonalcoholic fatty liver disease activity score, and/or decreased lobular inflammation), improves lipid profile parameters (e.g., LDL, HDL, ApoB, TG improved), decreases elevated liver enzyme levels, decreases steatosis, decreases fibrosis and/or induced acute hepatitis, increases insulin signaling (PI3K-AKT and/or IRS-1p), decrease inflammatory markers (e.g., TNF-α, IL-1b, IL-6, CRP, NF-kB, PGE-2, iNOS, MCP-1, MPO, ERK, JNK, and/or COX-2), decreases cartilage degradation, and/or increases FOXO3 mRNA levels. Some specific disease states contemplated for use of the disclosed compounds and salts include cardiovascular inflammation, dyslipidemia, hypertriglyceridemia, inflammation, liver disease, reperfusion injury, and reduction of platelet aggregation.

Dosing

The compounds or salts disclosed herein are useful in, e.g., methods of reducing CRP and modifying the levels of inflammatory biomarkers, as described herein, and is thus believed to be useful in methods of treating or preventing a CVD, supporting cardiovascular health, and supporting inflammatory health. For purposes of the disclosure, the amount or dose of the compound or salt administered should be sufficient to effect, e.g., a therapeutic or prophylactic response, in the subject or animal over a reasonable time frame. For example, the dose should be sufficient to treat a CVD by way of reducing CRP levels as described herein in a period of from about 1 to 4 minutes, 1 to 4 hours or 1 to 4 weeks or longer, e.g., 5 to 20 or more weeks, from the time of administration. In certain embodiments, the time period could be even longer. In some aspects, the effect is demonstrated within 1 to 2 weeks, within 4 weeks, within 8 weeks, within 12 weeks, within 24 weeks, within 48 weeks, or within 60 weeks.

The dose will be determined by the efficacy of the particular formulation and the condition of the animal (e.g., human), as well as the body weight of the animal (e.g., human) to be treated.

The dose also will be determined by the existence, nature and extent of any adverse side effects that might accompany the administration of a particular active agent of the present disclosure. Typically, the attending physician will decide the dosage of the active agent of the present disclosure with which to treat each individual patient, taking into consideration a variety of factors, such as age, body weight, general health, diet, sex, active agent of the present disclosure to be administered, route of administration, and the severity of the condition being treated. By way of example and not intending to limit the present disclosure, the dose of the compound or salt of the present disclosure can be about 0.0001 to about 1 g/kg body weight of the subject being treated/day, from about 0.0001 to about 0.001 g/kg body weight/day, or about 0.01 mg to about 1 g/kg body weight/day.

Combinations

In some embodiments, the compound or salt as disclosed herein is administered alone, and in alternative embodiments, the compound or salt as disclosed herein is administered in combination with another therapeutic agent. In some aspects, the other therapeutic agent aims to treat or prevent a cardiovascular disease. In exemplary aspects, the other agent is a statin, a hypertension medication, niacin, fibrate, cholesterylester transfer protein (CETP) inhibitor, an anti-diabetic agent, or a vasoactive agent. The statin in some aspects is atorvastatin, fluvastatin, lovastatin, pravastatin, simvastatin, or rosuvastatin. The hypertension medication may be any of those described herein. The CETP inhibitor may be, e.g., torcetrapib, dalcetrapib, evacetrapib, obicetrapib, or anacetrapib. The anti-diabetic agent may be any of those described herein. The vasoactive agent may be an inotrope which increases myocardial contractility, a vasopressor which causes vasoconstriction leading to increased systemic and/or pulmonary vascular resistance, an inodilator which causes vasodilation leading to decreased systemic and/or pulmonary vascular resistance. The inotrope may be, e.g., adrenaline, dobutamine, isoprenaline, and ephedrine. In some aspects, the vasopressor is noradrenaline, vasopressin, metaraminol, or methylene blue. In certain instances, the inodilator is milrinone or levosimendan. In exemplary instances, the vasoactive agent is dopamine. In some aspects, the vasoactive agent is a catecholamine, e.g., adrenaline, noradrenaline, phenylephedrine and metaraminol, ephedrine, dopamine, dobutamine, isoprenaline. In some aspects, the vasoactive agent is levosimendan or milrinone.

In exemplary aspects, the compound or salt as disclosed herein is administered in combination with a hypertension medication, including, but not limited to, a diuretic, a beta blocker, an ACE inhibitor, a angiotensin receptor blocker, a calcium channel blocker, an alpha blocker, an alpha-2 receptor agonist, a central agonist, a renin inhibitor, an arterial vasodilator, and the like. In some aspects, the diuretic is any drug that increases urination to reduce sodium and fluid in the body and optionally is selected from the group consisting of: bumetanide, chlorthalidone, chlorothiazide, ethacrynate, furosemide, hydrochlorothiazide HCTZ (Esidrix, hydrodiuril, microzide), indapamide, methclothiazide, metolazone, torsemide, amilioride, spironolactone, triamterene, amiloride hydrochloride. In exemplary aspects, the beta blocker is any that act directly on the heart to reduce heart rate, force of pumping, and blood volume. In some aspects, the beta blocker is acebutolol, atenolol, bisoprolol fumarate, carvedilol, esmilol, labetalol, metoprolol tartrate, metoprolol succinate, nadolol, nebivolol, penbutolol sulfate, propranolol, or sotalol. In some aspects, the ace inhibitor is benazepril hydrochloride, captopril, enalapril maleate, fosinopril sodium, lisinopril, moexipril, perindopril, quinapril, ramipril, or trandolapril. In some instances, the angiotensin II receptor blocker is azilsartan, candesartan, eprosartan mesylate, irbesartan, losartan potassium, olmesarten, telmisartan, valsartan. In some instances, the calcium channel blocker is amlodipine besylate, clevidipine, diltiazem hydrochloride, felodipine, isradipine, nicardipine, nifedipene, nimodipine, nisoldipine, verapamil hydrochloride. In some regards, the alpha blocker is doxazosin mesylate, prazosin hydrochloride, or terazosin hydrochloride. In certain aspects, the alpha-2 receptor agonist is methyldopa. In certain aspects, the central agonist is clonidine hydrochloride and guanfacine hydrochloride. In some instances, the hypertension medication is a peripheral adrenergic inhibitor, such as hyanadrel, guanethidine monosulfate, or reserpine. In certain instances, the vasodilator is minoxidil or hydralazine.

In exemplary aspects, the compound or salt as disclosed herein is administered in combination with an anti-diabetic or anti-obesity agent. Anti-diabetic agents known in the art or under investigation include insulin, leptin, Peptide YY (PYY), Pancreatic Peptide (PP), fibroblast growth factor 21 (FGF21), Y2Y4 receptor agonists, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; glucokinase activators (GKA); glucagon receptor antagonists (GRA); or FBPase (fructose 1,6-bisphosphatase) inhibitors. Anti-obesity agents known in the art or under investigation include appetite suppressants, including phenethylamine type stimulants, phentermine (optionally with fenfluramine or dexfenfluramine), diethylpropion (Tenuate®), phendimetrazine (Prelu-2®, Bontril®), benzphetamine (Didrex®), sibutramine (Meridia®, Reductil®); rimonabant (Acomplia®), other cannabinoid receptor antagonists; oxyntomodulin; fluoxetine hydrochloride (Prozac); Qnexa (topiramate and phentermine), Excalia (bupropion and zonisamide) or Contrave (bupropion and naltrexone); or lipase inhibitors, similar to XENICAL (Orlistat) or Cetilistat (also known as ATL-962), or GT 389-255.

In exemplary aspects, the compound or salt as disclosed herein is administered in combination with an agent for treatment of non-alcoholic fatty liver disease or NASH. Agents used to treat non-alcoholic fatty liver disease include ursodeoxycholic acid (a.k.a., Actigall, URSO, and Ursodiol), Metformin (Glucophage), rosiglitazone (Avandia), Clofibrate, Gemfibrozil, Polymixin B, and Betaine.

Cardiovascular Diseases and Cardiovascular Health

The present disclosure provides methods of preventing or treating cardiovascular disease (CVD) in a subject. In exemplary embodiments, the methods prevent or treat CVD by reducing C-reactive protein (CRP) levels. In exemplary embodiments, the method comprises administering a therapeutically effective amount of the compound or salt to the subject. In some embodiments, the subject is one who also receives a standard of care for CVD or CVD risk management.

The present disclosure also provides methods of supporting cardiovascular health in a subject at risk for or suffering from CVD. In exemplary embodiments, the methods support cardiovascular health by reducing CRP levels. In exemplary embodiments, the method comprises administering the compound or salt to the subject. In some embodiments, the subject is one who also receives a standard of care for CVD or CVD risk management. As used herein, the term "cardiovascular health" refers to the healthy structure or function of the heart and blood vessels.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating CVD of the present disclosure can provide any amount or any level of treatment. Furthermore, the treatment provided by the method of the present disclosure can include treatment of one or more conditions or symptoms or signs of the CVD being treated. Also, the treatment provided by the methods of the present disclosure can encompass slowing the progression of the CVD. For example, the methods can treat CVD by virtue of reducing build-up of plaque on the artery walls, treating angina, dyspnea, or nausea, managing CVD or signs or symptoms thereof, and the like. As used herein, the term "prevent" as well as word related thereto refers to delaying the onset or recurrence of the CVD by at least 1 day, 2 days, 4 days, 6 days, 8 days, 10 days, 15 days, 30 days, two months, 3 months, 4 months, 6 months, 1 year, 2 years, 3 years, 4 years, or more. In exemplary aspects, the methods treat or prevent by way increasing the survival of the subject.

As used herein, the term "cardiovascular disease" or "CVD" refers to a class of diseases involving the heart or blood vessels. CVD includes coronary artery diseases (CAD), e.g., as angina and myocardial infarction (commonly known as a heart attack), as well, as stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis. In some aspects, the CVD includes angina, arrhythmia, congenital heart disease, CAD, dilated cardiomyopathy, heart attack, heart failure, hypertrophic cardiomyopathy, mitral regurgitation, mitral valve prolapse, pulmonary stenosis, rheumatic heart disease. The CVD in exemplary aspects, involves the blood vessels and thus may be a vascular disease. Such vascular diseases include, but are not limited to: coronary artery disease, peripheral arterial disease, cerebrovascular disease, renal artery stenosis, aortic aneurysm, Raynaud's disease, Buerger's disease, peripheral venous disease, atherosclerosis, stroke, venous blood clots, and blood clotting disorders. The CVD in exemplary aspects, involves the heart and may be one of the following: cardiomyopathy, hypertensive heart disease, heart failure, pulmonary heart disease, cardiac dysrhythmias, an inflammatory heart disease (e.g., endocarditis, inflammatory cardiomegaly, myocarditis, eosinophilic myocarditis), a valvular heart disease, congenital heart disease, or rheumatic heart disease.

As used herein, the term "standard of care for CVD or CVD risk management" refers to any of the following agents which aims to treat or prevent a cardiovascular disease: a nitrate, a statin, a hypertension medication, niacin, fibrate, CETP inhibitor, an anti-diabetic agent, a vasoactive agent. In some aspects, the standard of care for CVD or CVD risk management is a nitrate or other anti-anginal therapeutic agent (e.g., a beta blocker, a calcium channel blocker). Such agents are described herein and also known in the art.

In exemplary aspects, the subject, prior to the administration of the compound or salt, exhibits a C-reactive protein (CRP) level of at least 2 mg/L, optionally, at least about 3 mg/L, at least about 4 mg/L, at least about 5 mg/L, at least about 6 mg/L, or more. In certain instances, the subject, following the administration of the compound or salt, exhibits a C-reactive protein (CRP) level below 2 mg/L, optionally, below about 1.9 mg/L, below about 1.8 mg/L, about 1.7 mg/L, about 1.6 mg/L, about 1.5 mg/L, about 1.4 mg/L, about 1.3 mg/L, about 1.2 mg/L, about 1.1 mg/L, about 1.0 mg/L, about 0.9 mg/L, about 0.8 mg/L, about 0.7 mg/L, about 0.6 mg/L, about 0.5 mg/L, about 0.4 mg/L, about 0.3 mg/L, about 0.2 mg/L, about 0.1 mg/L.

Methods of Reducing CRP

Also provided by the present disclosure are methods of reducing CRP in a subject. In exemplary embodiments, the method comprises administering the compound or salt to the subject. In exemplary embodiments of such methods of reducing CRP in a subject, the subject is at risk for or suffers from CVD.

As used herein, the phrase "reducing CRP levels" may refer to any decrease or reduction in CRP levels. The decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease. Methods of measuring CRP levels are known in the art and include the method described herein in Examples.

Inflammatory Health and Biomarkers Thereof

Further provided are methods of supporting inflammatory health in a subject at risk for or suffering from CVD. In exemplary embodiments, the methods prevent or treat CVD by reducing CRP levels. In exemplary embodiments, the method comprises administering the compound or salt to the subject. In some embodiments, the subject is one who also receives a standard of care for CVD or CVD risk management.

The present disclosure additionally provides methods of modifying levels of inflammatory health biomarkers or cardiovascular health biomarkers in a subject. In exemplary embodiments, the method (a) reduces levels of one or more of the following: tumor necrosis factor-α (TNF-α), Interleukin-1beta (IL-1β), Interleukin-6 (IL-6), Interferon (IFN-γ), oxidized LDL, total cholesterol, LDL cholesterol, VLDL cholesterol, triglycerides, HemoglobinA1c (HbA1c), alanine aminotransferase (ALT), Aspartate Aminotransferase (AST), body weight, or blood pressure; and/or (b) increases levels of Forkhead box O3 (FOXO3) activation or HDL cholesterol. In exemplary aspects, the method comprises administering the compound or salt as disclosed herein. In exemplary embodiments of such methods of modifying levels of biomarkers in a subject, the subject also receives standard of care for CVD or CVD risk management.

As used herein, the phrase "reduces levels" or "reducing levels" or similar phrase may refer to any decrease or reduction in level for the recited biomarker. The decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease. As used herein, the phrase "increases levels" or "increasing levels" or similar phrase may refer to any increase in level for the recited biomarker. The increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase.

Suitable methods of determining levels of protein biomarkers (e.g., TNF-α, IL-1β, IL-6, INF-γ, ALT, HbA1c, and AST) are known in the art and include immunoassays (e.g., Western blotting, an enzyme-linked immunosorbent assay (ELISA), a radioimmunoassay (RIA), and immunohistochemical assay) or bead-based multiplex assays, e.g., those described in Djoba Siawaya J F, Roberts T, Babb C, Black G, Golakai H J, Stanley K, et al. (2008) An Evaluation of Commercial Fluorescent Bead-Based Luminex Cytokine Assays. PLoS ONE 3(7): e2535. Proteomic analysis which is the systematic identification and quantification of proteins of a particular biological system are known. Mass spectrometry is typically the technique used for this purposes. Methods of measuring biomarker levels are described herein in Examples.

Methods of measuring oxidized low-density lipoprotein (LDL), total cholesterol, LDL cholesterol, very low-density lipoprotein (VLDL) cholesterol, triglycerides, FOXO3 activation or high-density lipoprotein (HDL) cholesterol are known in the art. See, e.g., Park et al., Oncotarget 7(27): 42110-42125 (2016); Chae et al. Sci Rep 8:284 (2018); Lei, et al., Front. Physiol. 7, 270 (2016); and Ghosh et al., Indian J Clin Biochem 21(1): 181-184 (2006).

The measurement of body weight may be accomplished using a scale. In some aspects, the measurement of blood pressure is accomplished by using a blood pressure monitor.

Subjects

In exemplary aspects, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human. In some aspects, the human is an adult aged 18 years or older. In some aspects, the human is a child aged 17 years or less.

In exemplary aspects, the subject is suffering from a CVD or has a medical history of suffering from CVD, or a sign or symptom thereof. In some aspects, the subject is diagnosed with a CVD. In some instances, the CVD is one of the CVD described herein. In exemplary aspects, the subject has (or had) one of more of the following: myocardial infarction, coronary artery bypass graft (CABG), angioplasty, an intracoronary artery stent, angina, stroke, transient ischemic attack, atherosclerotic carotid artery disease. In exemplary instances, the subject suffers from Diabetes Mellitus Type II, hypertension, hyperlipidemia, or obesity, or is a smoker. In some aspects, the subject is also administered one of more of the following cardiac therapeutics: a statin, a hypertension medication, niacin, fibrate, CETP inhibitor, an antidiabetic agent, a vasoactive agent. In some aspects, the method comprises a combination treatment comprising a compound or salt as disclosed herein and another therapeutic agent as described herein.

Synthesis

Compounds can be synthesized in using typical synthetic chemistry techniques using commercially available starting materials, compounds known in the literature, or from readily prepared intermediates, by employing standard synthetic methods and procedures either known to those of skill in the art, or in light of the teachings herein. Generally, the synthesis of the disclosed compounds can be achieved following a synthesis as shown in the below scheme.

Scheme

Astaxanthin di-conjugate 2 (Asta-DMG$_2$)

The astaxanthin and dimethylglycine or dimethylglycine acid chloride can be coupled together using a coupling reagent. Contemplated coupling reagents include PyBOP (benzotriazol-1-yl-oxytripyrrolidinophosphonium hexafluorophosphate) and EDC (1-(3-dimethylaminopropyl)-3-ethylcarbodiimide). The method can be performed optionally in the presence of a suitable base (e.g. triethylamine or di-isopropylethylamine). The method can be performed in a suitable solvent (e.g. tetrahydrofuran, dichloromethane or DMF).

The dimethylglycine compounds disclosed herein have an advantage in their synthesis since no protection of the amine group on the dimethylglycine need be introduced prior to coupling to the astaxanthin then removed after coupling. By using the dimethylglycine ester form, then, there are two fewer steps of the synthetic method compared to the sarcosine ester form, whose amine on the sarcosine must be protected prior to coupling with astaxanthin (e.g., using a Boc protecting group) then deprotected under acidic conditions to remove the protecting group after coupling to astaxanthin, as shown in the below scheme.

Scheme

S,S-Astaxanthin
(non-ionizable, insoluble, poor oral aborption)

Coupling with 2 eq of
Boc-protected amino acid

Boc-protected S,S-Astaxanthin amino acid diester

Boc-removal with HCl
to form di-amino acid ester
dihydrochloride salt

S,S-Astaxanthin amino acid diester
dihydrochloride salt
(Ionizable, water soluble, good oral aborption)

Examples

General Information: All chemical reagents were obtained from CombiBlocks or Oakwood Chemicals and used as is unless otherwise noted. The reagents obtained from CombiBlocks include Boc-Sar-OH (Lot #B73210), N,N-dimethylglycine (Lot #B31876), 1-methylimidazole (Lot #B29359), and EDC·HCl (Lot #B30205). 5-6M HCl in isopropanol (Lot #097797L02K) was obtained from Oakwood Chemicals. Dichloromethane (Lot #188784) and MTBE (Lot #178412) were obtained from Fisher Scientific and used as is unless otherwise noted. All reactions were carried out under nitrogen in flame-dried glassware using standard Schlenk techniques unless otherwise noted. Reactions were monitored by LCMS. Method info: Luna Omega 3.0 μm Polar C18 00 Å 4.6×150 mm (00F-4760-E0) column; water with 0.05% TFA (mobile phase A), acetonitrile with 0.05% TFA (mobile phase B); 40% to 94% increase of B over 10 min, 94% B for 17 min; 1.0 mL/min flow rate; 40° C. column temperature; 10 μL injection volume; monitoring at 474 nm. $^1$H, and $^{13}$C data were obtained using either 500 MHz Bruker AV-III (125 MHz 13C) spectrometer in CDCl$_3$ with 0.03% (v/v) TMS (Aldrich, Lot #MKCF4681) or methanol-d$_4$ (Aldrich, Lot #MBBC4451). Chemical shifts (δ) are reported in ppm and standardized with solvent as internal standard based on literature reported values.

Synthesis of Astaxanthin Sarcosine Diester (ADSa): A flame-dried 3-necked 100 mL round bottom flask wrapped in foil and fitted with a thermometer was cooled to room temperature under nitrogen. To the flask was charged 3S,3'S-astaxanthin (5 g, 8.3 mmol) followed by CH$_2$Cl$_2$ (100 mL). The solution was degassed, purged with nitrogen and placed in a brine/ice bath. The solution was cooled to 0° C.±1° C. To the solution was sequentially added boc-sarcosine (Boc-Sar-OH) (4.76 g, 25.1 mmol), 1-methylimidazole (2.02 mL, 25.1 mmol) and EDC.HCl (5.3 g, 27.6 mmol). The reaction mixture was stirred vigorously at 0° C. The reaction progress was monitored via LCMS. After 40 hrs, the reaction was quenched with 3:1:4 mixture of H$_2$O:brine:0.5 N HCl (100 mL). The phases were separated. The organic layer was washed with a 1:1:2 mixture of H$_2$O:brine:sat. NaHCO$_3$ (2×0 mL), then washed with H$_2$O (2×50 mL). The organic layer was collected, dried over MgSO$_4$, filtered through Whatman filter paper and concentrated in vacuo. The residual is dried under Hi-Vac to give DiBocSar Diester Astaxanthin, which was used in the subsequent step without further purification. $^1$H NMR (500 MHz, CDCl$_3$) δ 6.72-6.61 (m, 5H), 6.50-6.38 (m, 5H), 6.35-6.27 (m, 5H), 6.26-6.17 (m, 3H), 5.63-5.54 (m, 2H), 4.38-4.30 (m, 1H), 4.29 (s, 1H), 4.14-4.01 (m, 2H), 3.22 (s, 3H), 2.99 (s, 6H), 2.20-2.11 (m, 1H), 2.11-2.02 (m, 4H), 2.00 (d, J=4.5 Hz, 16H), 1.96 (s, 3H), 1.89-1.76 (m, 2H), 1.48 (d, J=6.0 Hz, 19H), 1.36 (d, J=9.3 Hz, 6H), 1.33 (s, 2H), 1.27-1.21 (m, 8H), 1.20 (s, 10H); $^{13}$C NMR (126 MHz, CDCl$_3$) δ 200.40, 193.76, 193.34, 169.42, 169.39, 162.21, 160.84, 160.73, 156.21, 155.53, 142.35, 142.32, 139.73, 136.71, 135.22, 135.19, 135.17, 134.57, 134.49, 133.84, 130.69, 128.23, 128.16, 126.80, 124.62, 123.30, 123.11, 123.04, 80.16, 80.02, 72.77, 71.70, 69.20, 50.90, 50.19, 49.44, 45.43, 42.62, 42.49, 37.16, 37.12, 36.80, 35.56, 35.39, 30.74, 30.46, 28.35, 28.29, 26.98, 26.38, 26.28, 26.15, 14.07, 14.00, 12.82, 12.58; MS (LCMS) 961.7 (M+Na$^+$); K$_f$ 0.62% H$_2$O.

To diBocSar diester astaxanthin (6.2 g, 6.7 mmol) dissolved in CH$_2$Cl$_2$ (18 mL) was added 5.0-6.0 M HCl in IPA (25 mL). The reaction was stirred vigorously at room temperature. The reaction progress was monitored via LCMS. After 22 hrs, the solvent was evaporated. The resulting solid was washed with 4:1 MTBE:CH$_2$Cl$_2$ (50 mL) and dried. The resulting solid was suspended in 4:1 MTBE:CH$_2$Cl$_2$ (50 mL) and stirred at room temperature. After 1 hr, the suspension was filtered over Whatman filter paper and dried under vacuum to give ADSa dihydrochloride salt. LCMS is consistent with product. $^1$H NMR (500 MHz, Methanol-d$_4$) δ 6.79-6.70 (m, 4H), 6.56 (s, 1H), 6.55-6.51 (m, 2H), 6.50 (s, 1H), 6.40 (s, 1H), 6.39-6.34 (m, 4H), 6.32 (s, 1H), 5.69 (dd, J=13.2, 6.3 Hz, 2H), 4.13 (s, 4H), 3.97-3.89 (m, 1H), 3.32 (s, 2H), 2.84 (s, 6H), 2.21-2.08 (m, 4H), 2.06-1.96 (m, 12H), 1.92 (d, J=0.8 Hz, 6H), 1.41 (s, 6H), 1.29 (s, 7H), 1.17 (d, J=6.1 Hz, 5H); $^{13}$C NMR (126 MHz, Methanol-d$_4$) δ 193.22, 165.79, 162.44, 142.79, 139.81, 136.54, 135.45, 134.32, 133.83, 130.66, 127.34, 124.44, 122.66, 73.08, 63.36, 41.85, 36.96, 32.25, 29.42, 25.08, 23.88, 12.92, 11.47, 11.17; MS (LCMS) 739.6 (M+H-2HCl$^+$).

Figure 1:
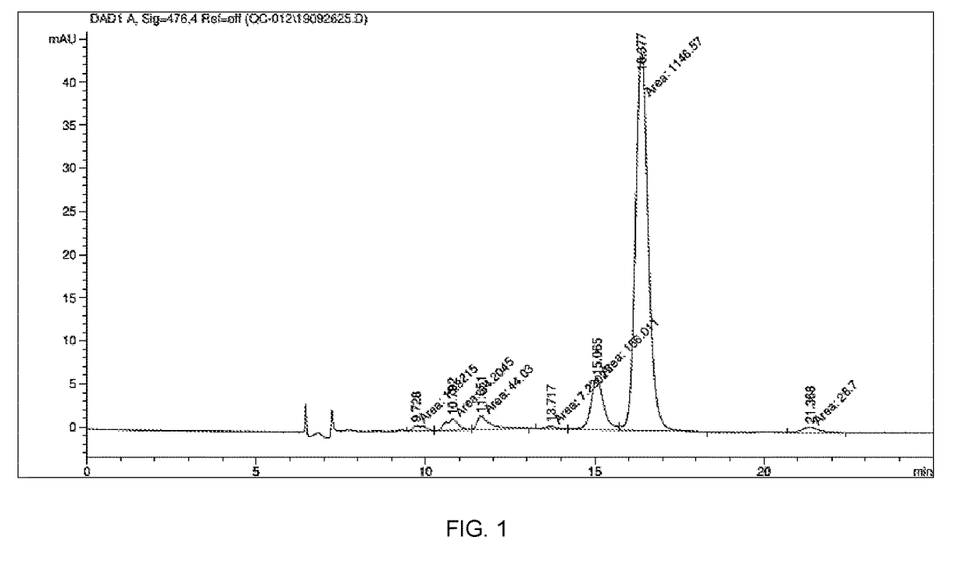
FIG. 1 shows a chromatogram of a disarcosine diester of astaxanthin as prepared herein.

The purity of the ADSa diHCl salt was assessed using HPLC, which is shown in FIG. 1, using the following HPLC conditions.

| Parameter | Description |
| --- | --- |
| Column | CHIRALPAK IB 5.0 μm |
| Column Dim. | 4.6 × 250 mm |
| Column P/No | 81325 |
| Mobile Phase | 95:5 v/v MtBE:MeOH w/0.1% ethylene diamine |
| Diluent | Ethanol |
| Program Type | Isocratic |
| Injection Run Time: | 25 min |
| Flow Rate: | 0.5 mL/min |
| Column Temperature: | 40° C. |
| Auto-sampler Temperature: | Ambient (5° C. if available) |
| Injection Volume: | 2 μL |
| Target Concentration: | 0.05 mg mL$^{-1}$ |
| Needle Wash | Ethanol |
| Detection Wavelength (DAD only) | 474 nm |
| Bandwidth (DAD only) | 4 nm |
| Reference Wavelength (DAD only) | None |
| Slit Width (DAD only) | 4 nm |
| Spectrum (DAD only) | Range: 190 to 600 nm |

Synthesis of Astaxanthin Dimethyl Glycinate Diester (ADMG): A flame-dried 250 mL round bottom flask wrapped in foil was cooled to room temperature under nitrogen. To the flask was charged with 3S,3'S-astaxanthin (5 g, 8.3 mmol) followed by CH$_2$Cl$_2$ (100 mL). The solution was degassed, purged with nitrogen and placed in a brine/ice bath. The solution was cooled to 0° C.±1° C. To the solution was sequentially added dimethylglycine (2.59 g, 25.1 mmol), 1-methylimidazole (2.02 mL, 25.1 mmol), and EDC·HCl (5.3 g, 27.6 mmol). The reaction mixture was stirred vigorously at 0° C. and allowed to warm to room temperature over time. The reaction progress was monitored via LCMS. After 16 hrs, LCMS analysis showed 100% conv with a ~94% diDMG ester and ~2% monoDMG ester. The reaction was quenched with 3:1:4 mixture of H$_2$O:brine:0.5 N HCl (100 mL). The phases were separated. The organic layer was washed with a 1:1:2 mixture of H$_2$O:brine:sat. NaHCO$_3$ (2×50 mL), then washed with H$_2$O (2×50 mL). The organic layer was collected, dried over MgSO$_4$, filtered through Whatman filter paper and concentrated in vacuo. The residual was taken up into MTBE and the solvent was concentrated in vacuo. This was repeated twice. The residual was dried under Hi-Vac to give the ADMG. MS (LCMS) 767.6 (M+H$^+$).

Crystallization of ADMG: A 250 mL round bottom flask was charged with ADMG (6 g, 7.8 mmol) followed by acetone (48 mL). The solution was purged with nitrogen and heated to 35° C. The temperature was maintained at 35° C. for 20 min. The temperature was decreased to 25° C. over 1.5 hrs. The solution was placed in a brine/ice-bath and cooled to 0° C. The temperature was maintained at 0° C. for 2 hrs. The resulting solids were filtered over Whatman filter paper, and washed with ice-cold acetone (6 mL). The solids were dried under Hi-vac to give ADMG. $^1$H NMR (500 MHz, CDCl$_3$) δ 6.70-6.68 (m, 1H), 6.68-6.66 (m, 1H), 6.66-6.63 (m, 1H), 6.48 (s, 1H), 6.44 (d, 2H), 6.40 (s, 1H), 6.34-6.30 (m, 3H), 6.30 (s, 1H), 6.23 (s, 1H), 6.20 (s, 1H), 5.61 (dd, J=14.1, 5.5 Hz, 2H), 3.35 (dd, J=30, 15 Hz, 4H), 2.44 (s, 12H), 2.13 (dd, J=14.1, 12.4 Hz, 2H), 2.07-1.95 (m, 14H), 1.91 (s, 6H), 1.24 (s, 6H); $^{13}$C NMR (126 MHz, CDCl$_3$) δ 193.75, 170.12, 160.68, 142.29, 139.72, 136.71, 135.15, 134.51, 133.83, 130.68, 128.29, 124.61, 123.12, 77.31, 77.05, 76.80, 71.20, 60.45, 45.30, 42.62, 37.14, 30.48, 26.35, 14.10, 12.82, 12.59, 0.01; MS (LCMS) 767.6 (M+H$^+$).

A flame-dried 250 mL round bottom flask wrapped in foil was cooled to room temperature under nitrogen. To the flask was charged with ADMG (3.3 g, 4.3 mmol) followed by CH$_2$Cl$_2$ (9 mL). The solution was degassed, and purged with nitrogen. The reaction was stirred vigorously at room temperature. After 1 hr, the solvent was evaporated. The residual was dried under Hi-vac to give a solid. The resulting solid was suspended in 4:1 MTBE:CH$_2$Cl$_2$ (15 mL). The suspension was stirred at room temperature. After 1 hr, the suspension was filtered over Whatman filter paper, washed with MTBE (15 mL), then washed with CH$_2$Cl$_2$ (15 mL) and dried under vacuum. The retained solids were suspended in 4:1 MTBE:CH$_2$Cl$_2$ (15 mL), stirred, filtered, washed and dried in the same fashion 2 additional times to give ADMG 2×HCl. $^1$H NMR (500 MHz, Methanol-d$_4$) δ 6.78-6.69 (m, 4H), 6.56 (s, 1H), 6.55-6.51 (m, 2H), 6.50 (s, 1H), 6.40 (s, 1H), 6.39-6.33 (m, 4H), 6.32 (s, 1H), 5.70 (dd, J=13.5, 6.1 Hz, 2H), 4.86 (s, 4H), 4.32 (s, 4H), 3.07 (s, 12H), 2.22-2.15 (m, 3H), 2.14-2.10 (m, 1H), 2.02 (d, J=14.0 Hz, 12H), 1.92 (s, 6H), 1.42 (s, 6H), 1.29 (s, 6H), 1.20 (s, 1H); $^{13}$C NMR (126 MHz, Methanol-d$_4$) δ 193.05, 165.04, 162.48, 142.81, 139.83, 136.55, 135.48, 134.33, 133.86, 130.68, 127.27, 124.45, 122.66, 73.37, 56.69, 43.15, 41.74, 36.98, 29.44, 25.84, 25.09, 12.95, 11.49, 11.19; MS (LCMS) 767.6 (M+H-2HCl$^+$).

Figure 2:
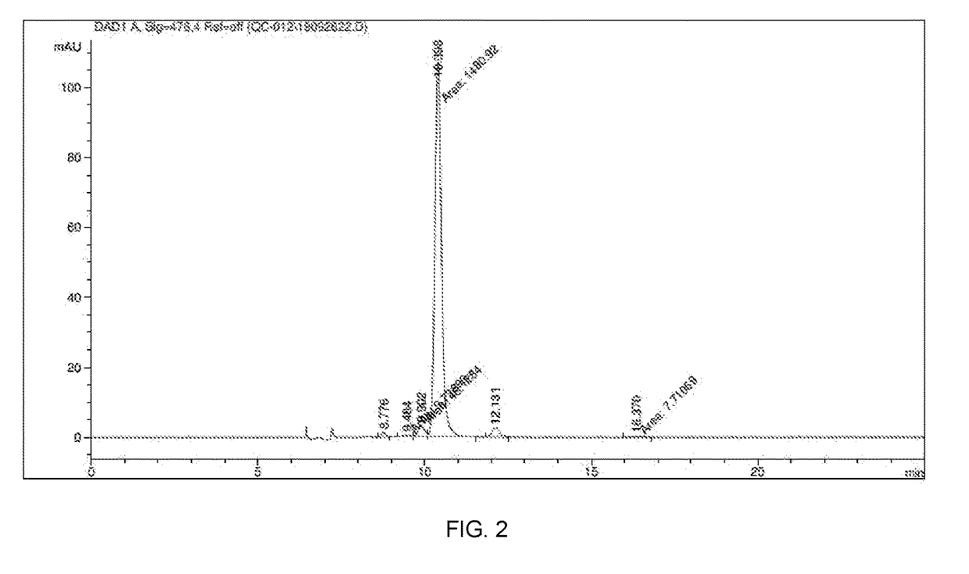
FIG. 2 shows a chromatogram of a dimethylglycine diester of astaxanthin as prepared herein.

The ADMG 2×HCl was assessed by chiral HPLC as shown in FIG. 2, using the same HPLC conditions as described for ADSa, above.

Conversion of ADMG to Astaxanthin: 0.65 mg of ADMG dihydrochloride salt was weighed into a 10 mL amber volumetric flask and diluted to volume with 8:1:1 (MeOH:DCM:water with 1 M KOH) which is approximately 1292 molar equivalents of KOH added. Analysis done via LCMS over time. The time between injections was 38 minutes and the complete conversion of ADMG to Astaxanthin likely occurred between the first injection (injection approximately 5 minutes after sample preparation) and the second injection (injection approximately 43 minutes after sample preparation). An impurity was identified by LC-MS and likely was an oxidation product of Astaxanthin and/or the ADMG monoester.

Hydrolysis of ADMG compared to ADSa in solution or under basic conditions: To a 10 mL brown bottle was added the ADMG 2HCl (5 mg) or ADSa 2HCl (5 mg) and methanol (1 mL), followed by adding saturated aq NaHCO$_3$ or Na$_2$CO$_3$ (0.5 mL) at rt. The mixture was stirred at room temperature or 50° C. The reaction was monitored by HPLC and LCMS after 16 hours. The results are shown in the below table, where A indicates starting diester (ADSa or ADMG), B indicates the hydrolyzed monoester, and C indicates free astaxanthin. "Byproduct" indicates a material that was formed other than the diester, monoester, or free astaxanthin.

| Ester | Base | Temp (° C.) | Result |
|---|---|---|---|
| ADSa | None | rt | 72% A |
|  |  |  | 16% byproduct |
|  | NaHCO$_3$ | rt | 7% A |
|  |  |  | 32% B |
|  |  |  | 51% C |
|  |  | 50 | 2% B |
|  |  |  | 90% C |
| ADMG | None | rt | 75% A |
|  |  |  | 21% byproduct |
|  | NaHCO$_3$ | rt | 64% A |
|  |  |  | 28% B |
|  |  |  | 2% C |
|  |  | 50 | 33% A |
|  |  |  | 50% B |
|  |  |  | 23% C |
|  | Na$_2$CO$_3$ | rt | 5% B |
|  |  |  | 90% C |
|  |  | 50 | 92% C |

Hydrolysis of ADMG compared to ADSa under basic conditions with KOH: To a 10 mL brown bottle was added the ADMG 2HCl or ADSa 2HCl and 9:1 methanol:dichloromethane to form a solution having a concentration of 100 µmol/L ADMG or ADSa. KOH was added at 55.6 molar equivalents as a solution in 81:9:10 methanol:dichloromethane:water at room temperature. The solution was analyzed using HPLC over various time points for starting diester (A), hydrolyzed monoester (B) and free astaxanthin (C). Byproduct indicates an impurity formed that is none of A, B, or C.

| Ester | Time (hr) | A | B | C | Byproduct |
|---|---|---|---|---|---|
| ADSa | 0 | 91.4% | 0.5% | 0% | 0% |
|  | 0.05 | 24.0% | 46.8% | 22.2% | 1.3% |
|  | 0.62 | 0% | 0.5% | 90.8% | 3.8% |
| ADMG | 0 | 93.7% | 0.1% | 0% | 0% |
|  | 0.07 | 86.4% | 7.3% | 0.1% | 0% |
|  | 0.65 | 36.1% | 44.9% | 13.2% | 0.1% |
|  | 1.23 | 14.4% | 44.6% | 34.6% | 0.8% |
|  | 1.80 | 5.5% | 34.2% | 53.0% | 1.4% |
|  | 2.38 | 2.0% | 23.4% | 66.6% | 2.0% |
|  | 2.97 | 0.7% | 14.9% | 75.4% | 2.7% |
|  | 3.55 | 0.2% | 9.2% | 80.7% | 3.4% |

What is claimed:

1. A compound having a structure:

or a pharmaceutically acceptable salt thereof.

2. The compound or salt of claim 1, having a structure:

3. The compound or salt of claim 1 as a hydrochloride salt.

4. The compound or salt of claim 3 as a dihydrochloride salt.

5. A composition comprising the compound or salt of claim 1 and a pharmaceutically acceptable excipient.

6. The composition of claim 5, having a stability of at least 90% by weight of compound or salt thereof after storage at room temperature for 1 week.

7. A method of preventing or treating cardiovascular disease in a subject by reducing C-reactive protein (CRP) levels comprising administering a therapeutically effective amount of the compound or salt of claim 1 to the subject, wherein the subject also receives standard of care for cardiovascular disease or risk management.

8. A method of supporting cardiovascular health in a subject at risk for or suffering from cardiovascular disease by reducing C-reactive protein (CRP) levels comprising administering the compound or salt of any one of claim 1 to the subject, wherein the subject also receives standard of care for cardiovascular disease or risk management.

9. A method of improving inflammatory health in a subject at risk for or suffering from cardiovascular disease by reducing C-reactive protein (CRP) levels comprising administering the compound or salt of claim 1 to the subject, wherein the subject also receives standard of care for cardiovascular disease or risk management.

10. The method of claim 7, wherein the subject, prior to the administration of the compound or salt, exhibits a C-reactive protein (CRP) level of at least 2 mg/L.

11. The method of claim 7, wherein the subject, following the administration of the compound or, exhibits a C-reactive protein (CRP) level below 2 mg/L.

12. A method of (a) reducing levels of one or more of the following: TNF-α, IL-1β, IL-6, INF-γ, oxidized LDL, total cholesterol, LDL cholesterol, VLDL cholesterol, triglycerides, HbA1c, ALT, AST, body weight, or blood pressure; or (b) increasing levels of FOXO3 activation and/or HDL cholesterol; in a subject comprising administering the compound or salt of claim 1, wherein the subject also receives standard of care for cardiovascular disease or risk management.

13. The method of claim 7, wherein the subject has (or had) one of more of the following: myocardial infarction, coronary artery bypass graft (CABG), angioplasty, an intra-coronary artery stent, angina, stroke, transient ischemic attack, atherosclerotic carotid artery disease.

14. The method of claim 7, wherein the subject suffers from Diabetes Mellitus Type II, hypertension, hyperlipidemia, or obesity, or is a smoker.

15. The method of claim 7, wherein the standard of care for cardiovascular disease or risk management comprises administration of a cardiac therapeutic agent.

16. The method of claim 7 wherein the standard of care for cardiovascular disease or risk management comprises administration of an anti-diabetic or anti-obesity agent.

17. The method of claim 7, wherein the effect is demonstrated within 24 weeks.

18. The method of claim 7. wherein the compound or salt is administered within about 30 minutes after food (e.g., a meal).

19. A method of making the compound or salt of claim 1 comprising admixing astaxanthin and dimethylglycine or dimethylglycine acid chloride optionally in the presence of a coupling agent to form the compound or salt thereof.

* * * * *

UNITED STATES PATENT AND TRADEMARK OFFICE
CERTIFICATE OF CORRECTION

| | | |
|---|---|---|
| PATENT NO. | : 12,338,209 B2 | Page 1 of 2 |
| APPLICATION NO. | : 17/764450 | |
| DATED | : June 24, 2025 | |
| INVENTOR(S) | : Henry L. Jackson et al. | |

It is certified that error appears in the above-identified patent and that said Letters Patent is hereby corrected as shown below:

In the Claims

Column 28, Lines 5-25, Claim 1, "  " should be

-- --.

Signed and Sealed this
Eighteenth Day of November, 2025

John A. Squires
*Director of the United States Patent and Trademark Office*

Columns 27 and 28, Lines 33-45, Claim 2,

" should be -- . --.

Column 28, Line 65, "any one of claim 1" should be -- claim 1 --.

Column 29, Line 11, "compound or," should be -- compound or salt, --.

Column 29, Line 23, "one of" should be -- one or --.

Column 30, Line 10, "claim 7" should be -- claim 7, --.

Column 30, Line 15, "claim 7." should be -- claim 7, --.